Figure 1A:
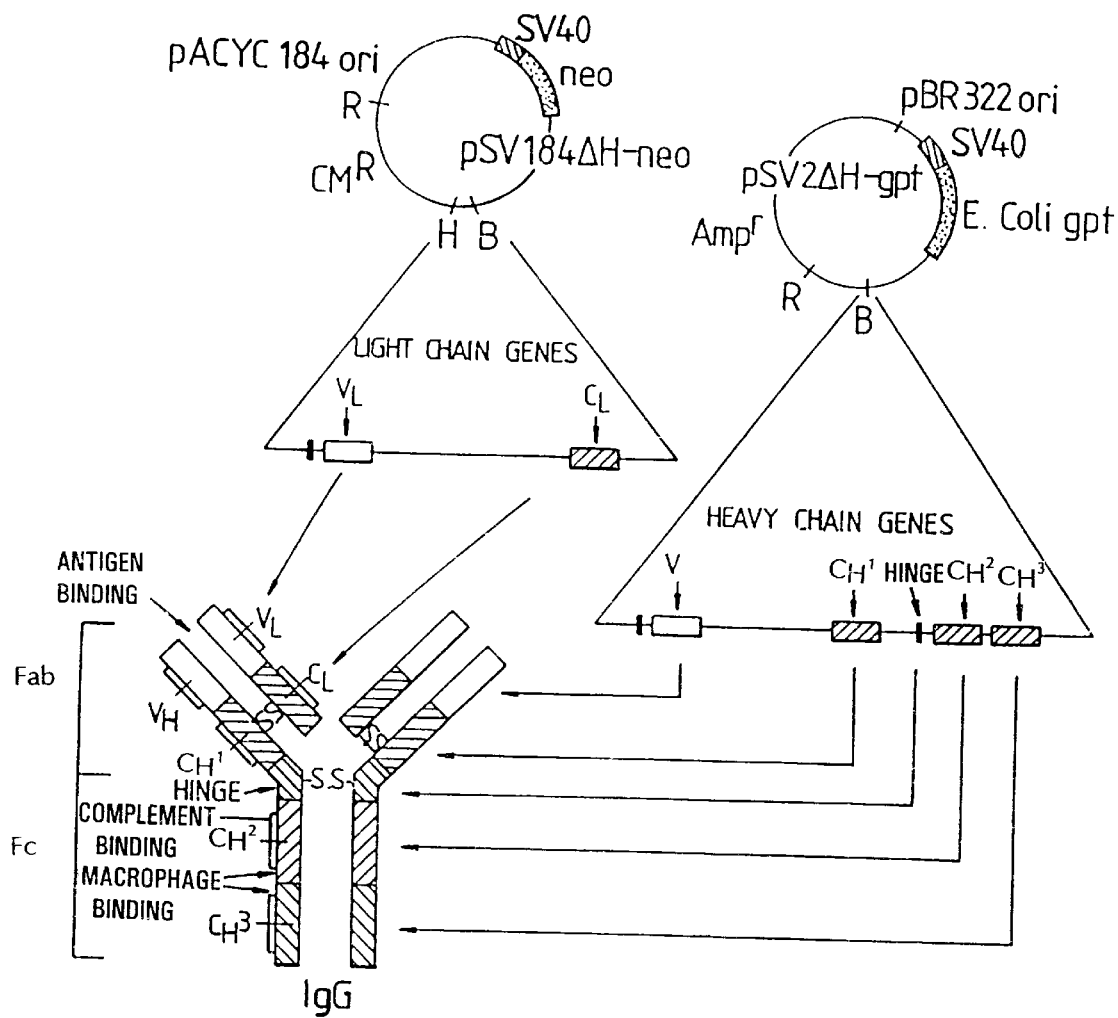

United States Patent [19]

Courtenay-Luck

[11] Patent Number: 6,107,469
[45] Date of Patent: *Aug. 22, 2000

[54] MINIMUM RECOGNITION UNIT OF A PEM MUCIN TANDEM REPEAT SPECIFIC MONOCLONAL ANTIBODY

[75] Inventor: Nigel Stephen Courtenay-Luck, London, United Kingdom

[73] Assignee: Cancer Therapeutics Limited, London, United Kingdom

[ * ] Notice: This patent is subject to a terminal disclaimer.

[21] Appl. No.: 09/131,052

[22] Filed: Aug. 7, 1998

Related U.S. Application Data

[62] Continuation of application No. 08/764,938, Dec. 13, 1996, Pat. No. 5,837,943, which is a continuation of application No. 08/122,546, filed as application No. PCT/GB92/00746, Apr. 23, 1992, Pat. No. 5,591,573.

[30] Foreign Application Priority Data

Apr. 23, 1991 [GB] United Kingdom ................ 9108652

[51] Int. Cl.$^7$ .......................... C07H 21/02; C07H 21/04; C07H 21/00
[52] U.S. Cl. ................. 536/23.1; 536/23.5; 536/23.53; 536/25.32
[58] Field of Search ................. 536/23.53, 23.1, 536/23.5, 25.32

[56] References Cited

U.S. PATENT DOCUMENTS 5,591,593   1/1997   Courtenay-Luck .

*Primary Examiner*—Mark Navarro
*Attorney, Agent, or Firm*—McAulay Nissen Goldberg & Kiel, LLP

[57] ABSTRACT

The peptide EPPT (Glu-Pro-Pro-Thr)(SEQ I YD NO: 1) selectively binds a mucin expressed by epithelial tumors. It may be incorporated into larger molecules, such as, peptides consisting of the sequence EPPT and further amino acids to form a peptide of up to 30 amino acids, and may be radiolabelled or used to guide toxins, etc. to cells expressing the mucin.

4 Claims, 4 Drawing Sheets

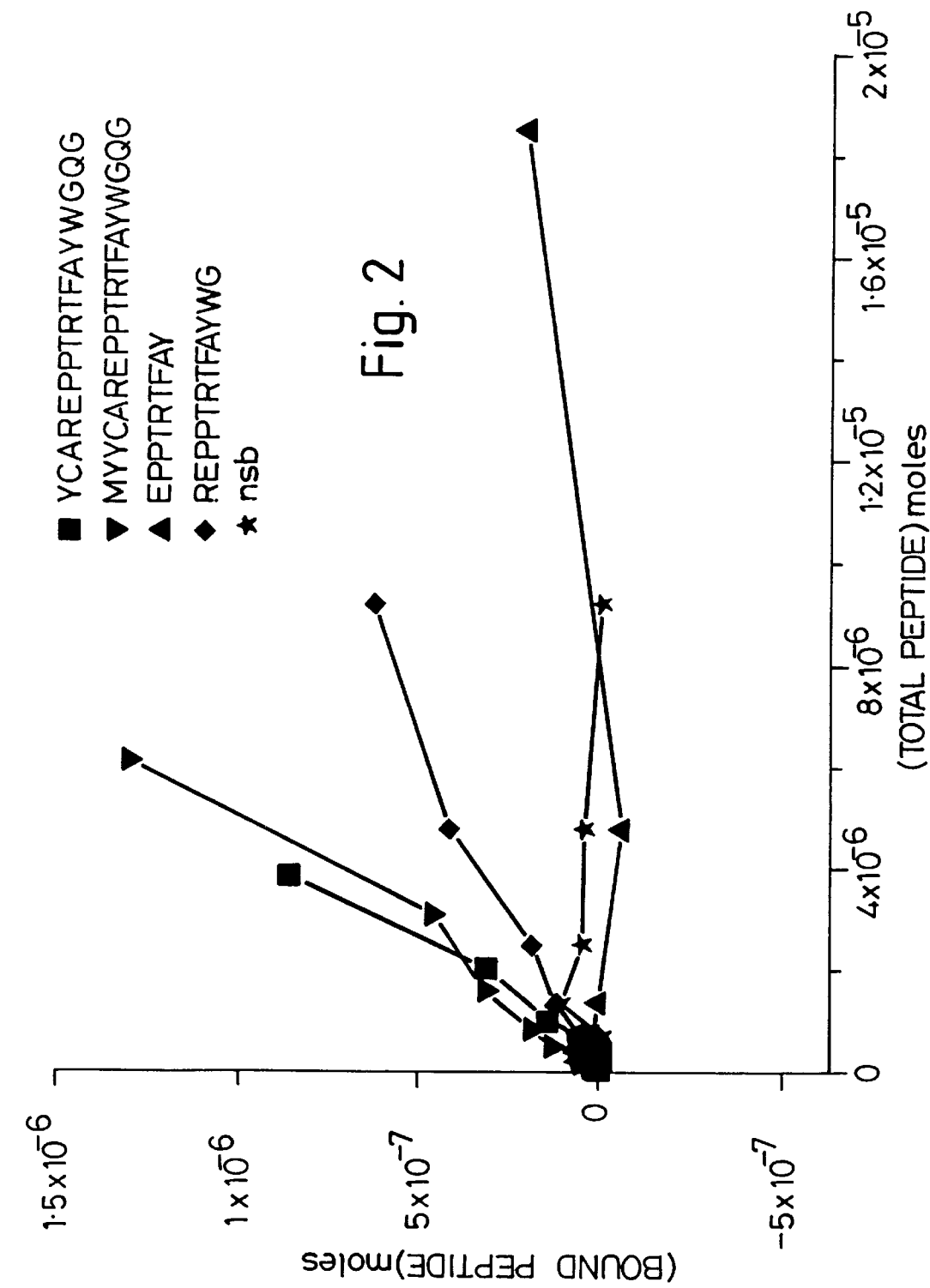

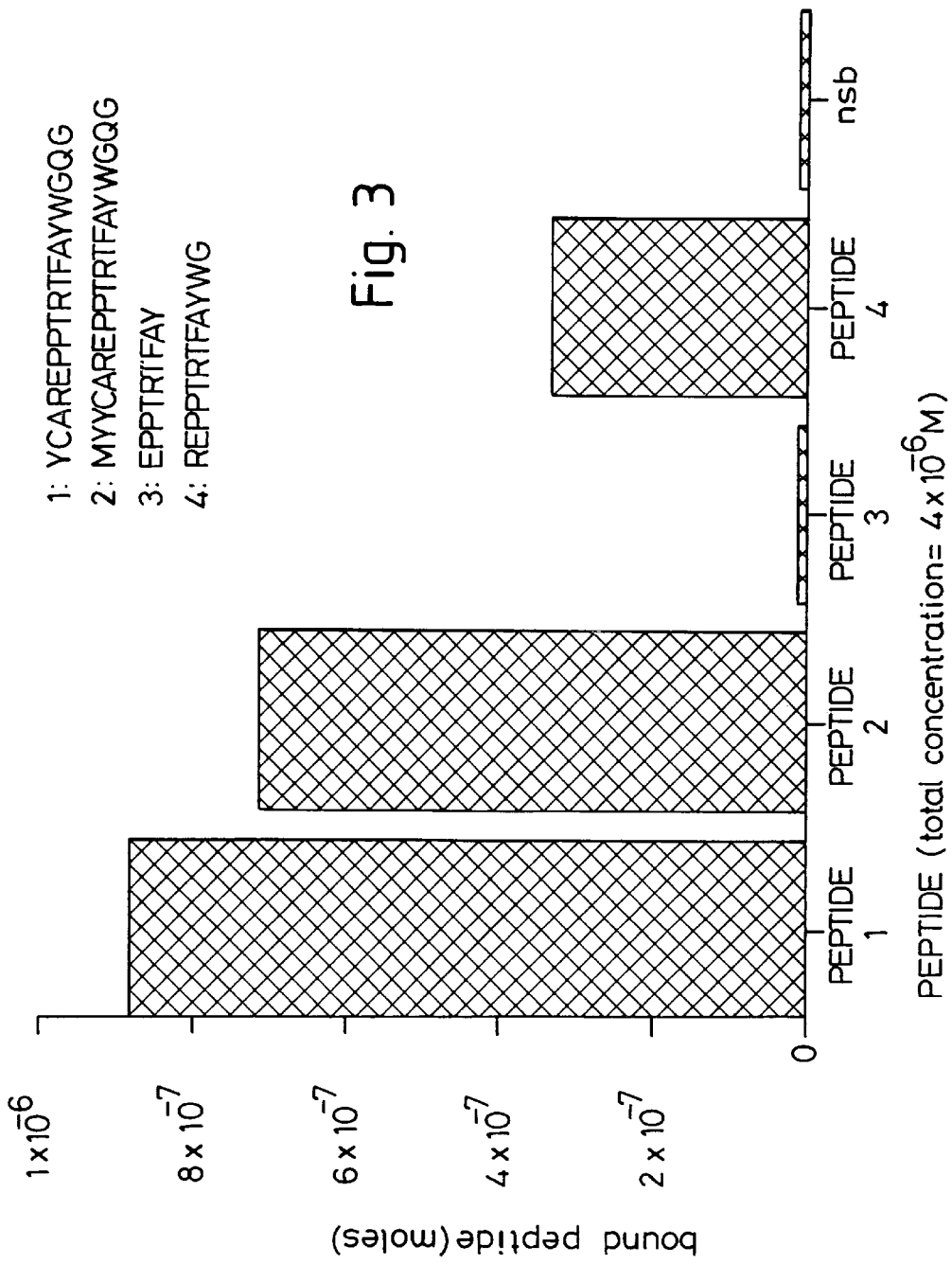

MINIMUM RECOGNITION UNIT OF A PEM MUCIN TANDEM REPEAT SPECIFIC MONOCLONAL ANTIBODY

This application is a continuation of Ser. No. 08/764,938, filed Dec. 13, 1996, now U.S. Pat. No. 5,833,943, which is a continuation of Ser. No. 08/122,546, filed Sep. 29, 1993, now U.S. Pat. No. 5,591,593, which is a National Phase of PCT/GB92/00746, filed Apr. 23, 1992.

The present invention relates to immunoreactive compounds; more specifically, it relates to genetically engineered antibodies.

Antibodies (Abs) are key molecules of the immune system. They provide defence against infection by microbial agents and are involved in a host of other immune reactions such as autoimmunity, allergies, inflammation, and graft rejection. Abs are unique in their specificity and are able to distinguish between very similar antigenic determinants of antigens. Because of this property, among others, antibodies are invaluable reagents for detecting, localizing and quantifying antigens.

Abs were initially obtained from immunized animals, but since different anti-sera represent different pools of heterogeneous Abs of varying specificities and isotypes, it was difficult to carry out reproducible studies using sera as the source of antibodies. It was then realized that large quantities of homogeneous Abs are produced in multiple myeloma, a tumour of plasma cells. Much of the information about the structure of immunoglobulins (Igs) was derived from studies using myeloma proteins. With the development of hybridoma technology, it became possible to generate an essentially endless supply of monoclonal antibodies (MAbs) of the desired specificities.

Antibodies are formed by polypeptide chains held together by non-covalent forces and disulfide bridges. A pair of identical light (L) chains (214 amino acids long) is linked to two identical heavy (H) chains to form a bilaterally symmetric structure (FIG. 1).

The polypeptide chains are folded into globular domains separated by short stretches of peptide segments; the H chain has four or five domains, depending on the isotype, and the L chain has two. The N-terminal portion of each chain constitutes the variable region ($V_H$, $V_L$). A $V_H$-$V_L$ pair carries the antigen combining site and contributes to antibody specificity. The rest of the chain forms the C region, the region of the molecule responsible for effector functions, such as $F_c$ receptor binding, complement fixation, catabolism and placental transport. Igs with different C regions and therefore of differing isotypes (in human they are IgM, IgD, IgGl-4, IgA2, and IgE) exhibit different biological properties. In most isotypes a hinge region separates $C_H1$ and $C_H2$ and provides the molecule with segmental flexibility. The enzyme papain cleaves near the hinge to generate the $F_{ab}$ and $F_c$ portions of the antibody molecule.

Murine MAbs are invaluable in research, but human Igs would be preferable for many applications, such as diagnosis and immune therapy, as they may interact more effectively with the patient's immune system. Because of the species difference, mouse Abs administered to humans can induce an immune response resulting in allergy, serum sickness or immune complex disease. These effects preclude repeated administration of MAb. It has also been demonstrated in clinical trials that host Abs neutralize the injected mouse MAbs and account for their rapid clearance. While mouse and rat hybridomas are easy to produce, attempts to make human MAbs have met with limited success. Mouse-human hybridomas are frequently genetically unstable, and the production of human/human hybrids has been hampered by the lack of suitable immortalized human cell lines and immunized human B cells. Due to ethical considerations, in vivo immunization of humans is very restricted.

Gene transfection provides an alternative method of producing MAbs. With this method it is now possible to produce not only wild-type Ig chains, but also novel Igs and mutants that have been constructed in vitro. Antibodies of the desired specificities, binding affinities, isotypes and species origin can be obtained by transfecting the appropriate genes into mouse myeloma or hybridoma cells in culture. Gene transfections circumvent many of the problems inherent in the hybridoma methodology. Since human or chimeric antibodies with the human constant (C) regions can be produced, the problem of immunogenicity can be avoided or minimized. Another advantage over mouse-human or human-human hybridomas is that the transfected mouse cells can be injected intra-peritoneally into mice, where they will proliferate and produce ascites from which large quantities of antibodies can be isolated.

The first chimeric mouse-human antibody made use of the rearranged and expressed V region genes from the myeloma S107 specific for phosphocholine. The $V_H$ was joined to human $C_\gamma 1$ or $C_\gamma 2$, and $V_L$ was joined to human Cκ [1]. When expressed together in the same cell, the heavy and light chains assembled into $H_2L_2$ tetramers that were secreted. This antibody bound antigen, and reaction with three monoclonal anti-idiotype antibodies verified that the polypeptide chains had folded appropriately to reproduce the antigen binding domains.

Experiments from the laboratory of Hozumi and his co-workers demonstrated that transfection of the rearranged murine TNP-specific $\mu$ and κ genes into plasmacytoma and hybridoma lines resulted in the production of pentameric IgM that bound hapten and triggered complement-dependent hemolysis [2, 3]. The TNP $V_H$ and $V_L$ genes were linked to human $C_\mu$ and $C_\kappa$ segments, respectively, to produce chimera IgM that again exhibited the properties of the wild-type mouse antibody [3, 4].

Two mouse-human chimaeric IgEs were produced that could trigger degranulation of mast cells when cross-linked by antigen on the cell membrane [5, 6].

To explore the potential of chimaeric antibodies in cancer therapy, an antibody was made that consists of the V regions derived from the mouse MAb 17–1A, which recognizes a tumour-associated surface Ag, and human $C_\gamma 3$ [7]. This chimaeric antibody had the same binding properties as the original mouse antibody.

Another chimaeric antibody with specificity for the surface antigen associated with certain human carcinomas was found to bind to human carcinoma cells [8].

Thus, murine variable regions were combined with human constant regions. A further step in the humanisation of rodent antibodies was the synthesis of hybrid variable regions in which the framework residues are of human origin and the complementarity-determining regions (CDRs) come from a mouse antibody. In the case of an NP-specific antibody, it was shown that the transfer of the CDRs from an anti-NP hybridoma onto the human framework of a human myeloma protein resulted in the transfer of antigen-specificity [9]. This result, obtained with a hapten antigen, was extended to antibodies directed against hen-egg lysozyme as well as a human T cell surface antigen [10, 11]. Thus, CDR grafting not only facilitates the construction of chimaeric antibodies but also allows the production of therapeutic reagents in which only the antibody CDR residues are of non-human origin.

CDR3 appears to be particularly important in determining the specificity of the antibody. Thus, Taub et al [52] showed that the specificity of an antibody to the platelet fibrinogen receptor was determined largely by the RYD sequence within the CDR3 of the antibody heavy chain. Williams et al [53] used a synthetic peptide from the light chain CDR2 of an antibody to inhibit the interaction of the antibody with its receptor. Conceptually, there is a "minimum recognition unit" of any given antibody, as discussed by Winter and Milstein [54].

We have now identified the minimum recognition unit of a murine monoclonal antibody specific for a mucin molecule associated with epithelial tumours, namely the amino acid sequence EPPT (Glu-Pro-Pro-Thr)(SEQ ID No 1).

One aspect of the present invention therefore provides a molecule comprising the amino acid sequence EPPT (SEQ ID No 1).

All peptides herein are written $H_2N \ldots COOH$ and the amino acids are the naturally-occurring L isomers.

The molecule of the invention may consist of the sequence EPPT (SEQ ID No 1). This short peptide may or may not be useful in its own right as a binding entity as discussed below but, if not useful in that way, may be used to prepare longer molecules of the invention which do bind the target entity. Preferably, the EPPT peptide includes further amino acids extending it in the N-terminal and/or C-terminal direction(s). For example, the peptide may be EPPTRTFAY (SEQ ID No 2), REPPTRTFAYWG (SEQ ID No 3) or MYYCAREPPTRTFAYWGQG (SEQ ID No 4) or any EPPT-containing fragment thereof. The peptide may be inserted in place of or form part of the CDR region (preferably CDR3) of an antibody variable framework region.

Preferably, the said variable framework region is human.

Thus, the peptide may form part of a (preferably human) antibody. Suitably, the peptide forms part of a complete (preferably human) $V_H$ or $V_L$ region and may additionally be associated with the remaining parts of the antibody to form a complete (preferably humanized) antibody. Alternatively, the peptide may form part of a smaller fragment of an antibody, such as an $F_{ab}$, $(F_{ab})_2$, $F_v$, $scF_v$ or dAb molecule. Further, the peptide may be expressed as part of a phage.

The isolated EPPT peptide itself, isolated EPPT-containing peptides of up to 30 amino acids in length, EPPT-containing polypeptides, proteins, antibody fragments and phages and EPPT-containing molecules generally are termed "molecules of the invention".

Such molecules are at their most useful when the EPPT moiety is exposed on the surface of the molecule and is available for interaction with other molecules. However, other such molecules which can be re-arranged in order to expose the EPPT moiety are also encompassed. For example, a molecule of the invention may be expressed as an insoluble protein in bacteria and then refolded in vitro for use in the methods of the invention.

The molecules of the invention may be used for a variety of purposes relating to the study or isolation and purification of the mucin to which they specifically bind and the imaging and treatment of cells exhibiting the mucin. For example, because the mucin is shed by the cell concerned, the molecule may be used in a diagnostic assay, based on blood or serum, for the presence of the cell in the body (eg using a radiolabelled version of the molecule to bind to antigen in the serum to compete for immobilised antigen with antigen-specific antibodies in the serum). In other embodiments, the molecule of the invention is coupled to a scintigraphic radiolabel, a cytotoxic compound or radioisotope, an enzyme for converting a non-toxic prodrug into a cytotoxic drug, a compound for activating the immune system in order to target the resulting conjugate to a desired cell type in the body, for example a tumour cell, or a cell-stimulating compound. Such conjugates have a "binding portion", which consists of the EPPT-containing molecule of the invention, and a "functional portion", which consists of the radiolabel, toxin or enzyme etc.

The molecule of the invention may alternatively be used alone (or, especially to increase in vivo stability, with an inert polypeptide addition, which may or may not form a complete antibody or antibody fragment with the said peptide) in order simply to block the activity of the mucin, particularly by physically interfering with its binding of another compound.

The binding portion and the functional portion of the conjugate (if also a peptide or polypeptide) may be linked together by any of the conventional ways of cross-linking polypeptides, such as those generally described in [18]. For example, one portion may be enriched with thiol groups and the other portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

The functional portion of the conjugate may be an enzyme for converting a non-toxic prodrug into a toxic drug, for example the conjugates of Bagshawe and his colleagues [19–21] or cyanide-releasing systems [22].

It may not be necessary for the whole enzyme to be present in the conjugate but, of course, the catalytic portion must be present. So-called "abzymes" may be used, where a monoclonal antibody is raised to a compound involved in the reaction one wishes to catalyse, usually the reactive intermediate state. The resulting antibody can then function as an enzyme for the reaction.

The conjugate may be purified by size exclusion or affinity chromatography, and tested for dual biological activities. The peptide immunoreactivity may be measured using an enzyme-linked immunosorbent assay (ELISA) with immobilised antigen and in a live cell radio-immunoassay. An enzyme assay may be used for β-glucosidase using a substrate which changes in absorbance when the glucose residues are hydrolysed, such as ONPG (o-nitrophenyl-β-D-glucopyranoside), liberating 2-nitrophenol which is measured spectrophotometrically at 405 nm.

Stability of the conjugate may be tested in vitro initially by incubating at 37° C. in serum, followed by size exclusion FPLC analysis. Stability in vivo can be tested in the same way in mice by analysing the serum at various times after injection of the conjugate. In addition, it is possible to radiolabel the peptide with $^{125}I$, and the enzyme with $^{131}I$ before conjugation, and to determine the biodistribution of the conjugate, free antibody and free enzyme in mice.

Alternatively, the conjugate may be produced as a fusion compound by recombinant DNA techniques whereby a length of DNA comprises respective regions encoding the two portions of the conjugate either adjacent one another or separated by a region encoding a linker peptide which does not destroy the desired properties of the conjugate. Conceivably, the two functional portions of the compound may overlap wholly or partly. The DNA is then expressed in a suitable host in known ways.

The conjugates may be administered in any suitable way, usually parenterally, for example intravenously, intraperitoneally or, preferably (for bladder cancers), intravesically (ie into the bladder), in standard sterile, non-pyrogenic formulations of diluents and carriers, for example isotonic saline (when administered intravenously). Once the conjugate has bound to the target cells and been cleared from the bloodstream (if necessary), which typically takes a day or so, the pro-drug is administered, usually as a single infused dose, or the tumour is imaged. If needed, because the conjugate may be immunogenic, cyclosporin or some other immunosuppressant can be administered to provide a longer period for treatment but usually this will not be necessary.

The timing between administrations of conjugate and pro-drug may be optimised in a non-inventive way since tumour/normal tissue ratios of conjugate (at least following intravenous delivery) are highest after about 4–6 days, whereas at this time the absolute amount of conjugate bound to the tumour, in terms of percent of injected dose per gram, is lower than at earlier times.

Therefore, the optimum interval between administration of the conjugate and the pro-drug will be a compromise between peak tumour concentration of enzyme and the best distribution ratio between tumour and normal tissues. The dosage of the conjugate will be chosen by the physician according to the usual criteria. At least in the case of methods employing a targeted enzyme and intravenous amygdalin as the toxic pro-drug, 1 to 50 daily doses of 0.1 to 10.0 grams per square metre of body surface area, preferably 1.0–5.0 g/m$^2$ are likely to be appropriate. For oral therapy, three doses per day of 0.05 to 10.0 g, preferably 1.0–5.0 g, for one to fifty days may be appropriate. The dosage of any conjugate will similarly be chosen according to normal criteria, particularly with reference to the type, stage and location of the tumour and the weight of the patient. The duration of treatment will depend in part upon the rapidity and extent of any immune reaction to the conjugate.

The conjugates, if necessary together with an appropriate pro-drug, are in principle suitable for the destruction of cells in any tumour or other defined class of cells selectively exhibiting the mucin recognised by the EPPT entity. This mucin appears to be expressed by a wide variety of epithelial tumours, including lung and breast tumours and tumours of the urinary tract, especially the bladder. The compounds are principally intended for human use but could be used for treating other mammals, including dogs, cats, cattle, horses, pigs and sheep.

The methods of the invention may be particularly suitable for the treatment of bladder carcinoma in situ, administering the antibody-enzyme conjugate and the amygdalin intravesically. Our studies on the administration of radiolabelled antibodies via this route indicate that high tumour/normal bladder ratios can be achieved, and that the antibody does not enter the circulation. Bladder cancer accounts for 2% of all human malignancies, of which approximately 70% of cases are superficial at the time of diagnosis. Recurrences occur in as many as 80% of cases after surgical resection, 10% of these progressing to a higher grade carcinoma with poorer prognosis.

The functional portion of the conjugate, when the conjugate is used for diagnosis, usually comprises and may consist of a radioactive atom for scintigraphic studies, for example technetium 99m ($^{99m}$Tc) or iodine-123 ($^{123}$I), or a spin label for nuclear magnetic resonance (nmr) imaging (also known as magnetic resonance imaging, mri), such as iodine-123 again, iodine-131, indium-111, fluorine-19, carbon-13, nitrogen-15, oxygen-17, gadolinium, manganese or iron.

When used in a compound for selective destruction of the tumour, the functional portion may comprise a highly radioactive atom, such as iodine-131, rhenium-186, rhenium-188 or yttrium-90, which emits enough energy to destroy neighbouring cells, or a cytotoxic chemical compound such as methotrexate, adriamicin, vinca alkaloids (vincristine, vinblastine, etoposide), daunorubicin or other intercalating agents.

The radio- or other labels may be incorporated in the conjugate in known ways. For example, the EPPT-containing peptide may be biosynthesized or may be synthesized by chemical amino acid synthesis using suitable amino acid precursors involving, for example, fluorine-19 in place of hydrogen. In such a compound, the CDR3 peptide incorporates the radio-label. Labels such as $^{99m}$Tc, $^{123}$I, $^{186}$Rh, $^{188}$Rh and $^{111}$In can be attached via a cysteine residue in the peptide. Yttrium-90 can be attached via a lysine residue. The IODOGEN method [23] can be used to incorporate iodine-123. Reference [24] describes other methods in detail.

Nucleotide coding sequences encoding the molecules of the invention (when the molecule is a peptide, polypeptide or protein) form further aspects of the invention, as do vectors and expression vehicles comprising such coding sequences, hosts including such vectors or expression vehicles (eg bacteria such as *E. coli*, yeasts such as *S. cerevisiae*, mammalian cells such as lymphoid cell lines (eg myeloma cells) and transgenic animals and plants, especially those in which the transgene is targeted for expression in cells other than B lymphocytes, and processes for preparing such molecules by culturing such hosts and isolating the molecules.

Thus, a further aspect of the invention provides a polynucleotide encoding an EPPT-containing peptide, polypeptide, protein or bacteriophage.

Such polynucleotides may be devised and created by known techniques such as those in the Sambrook et al manual [55]. In the specific case of "phage antibodies", ie bacteriophages including a part of an antibody (namely, in this case, the EPPT moiety), the techniques of McCafferty et al [56] may be used. Thus, the EPPT region may be expressed at the N-terminal region of the gene III protein of phage fd, since the gene III protein is normally expressed at the tip of the phage.

More specifically, an expressible polynucleotide coding sequence may be prepared by (i) providing a cell which comprises a first coding sequence encoding an EPPT-containing peptide, polypeptide or protein, (ii) obtaining DNA corresponding to the said coding sequence, and (iii) inserting the said DNA into a suitable expression cassette for the intended host.

Ways of carrying out step (i) are familiar from conventional immunological techniques and monoclonal antibody techniques. Essentially, an animal may be immunised with the antigen of interest, and immune system cells, for example spleen cells are isolated, optionally followed by immortalisation thereof by fusion with myeloma cells. Alternatively, based on more recent techniques, single B lymphocytes may be used or EBV-immortalised cells.

In step (ii) the specific EPPT-encoding DNA (or, more accurately, a copy thereof) may be isolated from the cell by PCR-based techniques, using primers known to be specific for variable framework regions. Further identical versions of such DNA may of course be made by PCR, chemical synthesis, reproduction in vivo or whatever method is convenient.

Step (iii) may be carried out by conventional recombinant DNA ligation techniques, using a promoter and other regulatory sequences suited to the intended host.

Figure 1B:
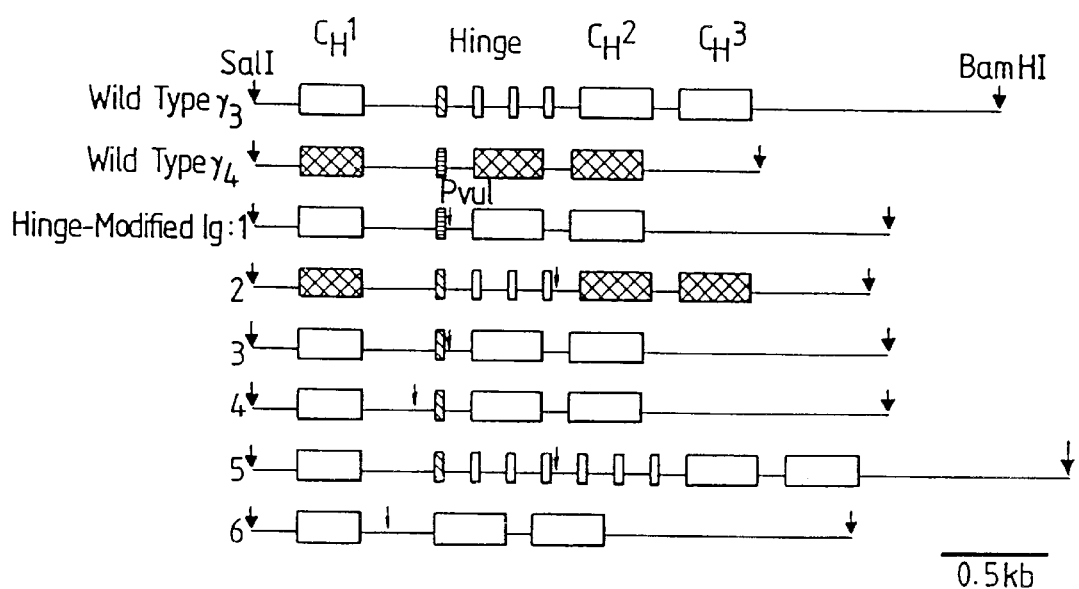

Embodiments of the invention and ways of putting the invention into practice will now be described in more detail, with reference to various examples and with reference to the accompanying figures, in which:

FIGS. 1A and 1B show the human γ constant region genes cloned as SalI–BamHI cassettes. $C_H1$, $C_H2$ and $C_H3$ exons of γ3 are indicated by empty boxes, and those of $γ_4$ by solid boxes. The hinge region of wild-type $γ_3$ is encoded by four exons: hinge exon 1 (hatched) is unique; exons 2, 3, 4, (shaded) are identical). Wild type $γ_4$ has a single hinge exon (cross-hatched). Thin arrows point to the StuI site in the intron that was converted to PvuI by the insertion of linkers. Hinge-modified constructs 1 and 2 show $γ_3$ and $γ_4$ with reciprocal hinge switches. 3–6 are modifications within $γ_3$; 3, $γ_3$ with hinge exon 1; 4, exon 4; 5, exons 1, 2, 3, 4, 2, 3, 4; and 6 no hinge.

FIG. 2 shows the binding of EPPT peptides to the immobilised mucin receptor peptide; and FIG. 3 shows the same data as FIG. 2, presented as a bar chart.

I. GENERAL TECHNIQUES

Expression of Antibody Coding Regions in Transfected Myeloma Cells

From 1983, several groups have described the introduction of DNA encoding an immunoglobulin heavy or light chain into a lymphoid cell line [25–28]. In all these cases, the genomic DNA encoding the immunoglobulin polypeptide was cloned into a gpt- or neo-based plasmid vector. The resultant plasmids were then introduced into the lymphoid cell lines either by use of co-precipitation with calcium phosphate or by DEAE-dextran facilitated DNA uptake or by fusing the lymphoid cells with spheroplasts made from the *Escherichia coli* that harboured the plasmid. Later, electroporation found wide use as an effective means of introducing DNA into a wide variety of cell-lines. From these and subsequent experiments, it is clear that the transfected gene is expressed in a manner appropriate to the cell type. In other words, in myeloma cells the transfected gene is heavily transcribed and good quantities of antibody are secreted; in pre-B and B cell lines, the introduced gene is expressed at much lower level and in non-lymphoid lines there is no correct expression of the introduced immunoglobulin gene. It is therefore clear that myelomas provide the ideal hosts for expressing transfected antibody genes as they not only recognize the immunoglobulin gene transcription signals and therefore produce the antibody in abundance but they are also well equipped for protein secretion.

Typically, the genes for the heavy and/or light chain of the desired antibody are cloned into a neo- or gpt-based plasmid. Ig genes to be used for transfection are cloned into eukaryotic expression vectors, the most commonly used of which are the pSV2 plasmids developed by Berg and co-workers [42–44]. These vectors contain a plasmid origin of replication and a marker for selection in bacteria, so large quantities of DNA can easily be obtained for genetic manipulations. Another essential feature of these vectors is a dominant marker selectable in eukaryotic cells; this marker is a bacterial gene transcribed under the control of the SV40 early region promoter. Included in this eukaryotic transcription unit 3' of the bacterial gene are SV40 sequences for splicing and polyadenylation. It is important that these are dominant selectable markers (markers that produce a selectable change in the phenotype of normal cells) so that they can be used in cell lines that have not been drug marked.

One of the selectable markers is the *Escherichia coli* gene encoding xanthine-guanine phosphor-ibosyltransferase (gpt). This enzyme, unlike the analogous endogenous enzyme, can use xanthine as a precursor for xanthine monophosphate, and permits cells provided with xanthine to survive in the presence of mycophenolic acid, a drug that blocks purine biosynthesis by preventing the conversion of inosine monophosphate to xanthine monophosphate. A second selectable marker is the neo gene from the transposon Tn5, which encodes a phosphotransferase that can inactivate the antibiotic G418. G418 interferes with the function of the 80S ribosome and blocks protein synthesis in eukaryotic cells.

The two plasmids pSV2gpt and pSV2neo (FIG. 1) contain the pBR322 origin of replication and the beta-lactamase gene for $Amp^R$. A more recently developed vector, pSV184neo, contains the $Cm^R$ gene and the origin of replication from the plasmid pACYC184 [45]. pBR and pACYC-derived plasmids are compatible, and so both can be propagated non-competitively within a bacterium. These vectors are not known to replicate as episomes in mouse cells but rather integrate into the chromosome. They are useful when stable transfectants are desired as a continuous source of antibody. In addition to the genes described above, pSV5 vectors contain the polyoma virus early region, which enables them to replicate to thousands of copies per mouse cell. The pSV5 vectors have only been employed for transient expression of immunoglobulin genes [46]. The exact extent of immunoglobulin gene DNA sequences that are required for maximal expression has not yet been fully determined. Initial experiments used complete genomic DNA with several kilobases of flanking sequence. However, most of the DNA that constitutes an antibody gene is, in fact, intron and much of this is probably dispensable. The major intron of the mouse heavy chain locus contains a transcription enhancer [29, 30, 26]; this enhancer can be removed from the intron and placed upstream of the immunoglobulin gene. Thus, much of the major intron of the immunoglobulin heavy chain gene can be deleted without any consequent loss of antibody yield after transfection [31]. There is at present no evidence that other introns within an immunoglobulin gene contain signals essential for antibody expression. However, experiments in which transcription of a μ heavy-chain cDNA is driven by a $V_H$ promoter/IgH enhancer combination have revealed that good expression requires the presence of an intron although this requirement is not specific for a particular intron [32]. Finally, in the context of immunoglobulin transcription signals, it should be noted that multicopy transfected Ig genes normally yield considerably less secreted antibody than is obtained from the single-copy endogenous gene in hybridomas. That this is also found in analogous experiments using transgenic mice strongly suggests that high level immunoglobulin gene expression requires sequence elements located beyond the region of DNA normally used in transfection experiments and which are therefore at some distance from the constant-region exons.

Expression in Transfectants of Non-lymphoid Cells

Expression of transfected Ig genes in lymphoid cell-lines can also be driven by non-immunoglobulin transcription signals. For example, promoters from a heat-shock gene or from SV40 or human cytomegalovirus have been used successfully [33–35]. The use of these transcription elements that are not lymphoid-specific appears to offer several advantages. The yields of antibody can be as good as those presently obtained with the $V_H$ promotor/IgH enhancer. [This, however, may reflect that the segments of genomic Ig genes used lack important transcription signals]. Furthermore, some viral transcription elements can allow good expression from Ig cDNA constructs without manifesting an intron requirement; this may prove of great use in the synthesis of modified antibodies or antibody fragments.

The use of viral and heat-shock promoters has allowed the synthesis of antibody by transfectants of non-lymphoid cell-lines to be evaluated. Success has been achieved with both IgM and IgG antibodies in non-lymphoid mammalian cell-lines [33–35]. Indeed, if the pattern of glycosylation is not severely affected, non-lymphoid hosts may be used for the expression of engineered antibodies.

Expression in Transgenic Animals

The introduction of immunoglobulin gene DNA into the mouse germline [36] illustrates the use of transgenic animals for the production of monoclonal antibodies. The gene for a chimaeric human IgA2 antibody may be introduced into the mouse germline [39]. The transgenic mice contain good levels of the chimaeric antibody in serum (about 100 μg/ml) and the antibody was also secreted in colostrum and milk.

Expression in *Escherichia coli* and Yeast

References 38 and 39 disclose bacterial expression systems for the synthesis of antibody fragments ($F_v$, $F_{ab}$ and the $F_c$ of IgE). Thus, there are now many expression systems available for the production of engineered antibodies although the technology will obviously continue to develop.

Making Chimaeric Antibodies with Human Effector Functions

The in vitro manipulation of immunoglobulin gene DNA prior to its introduction into myeloma cells allows the production of chimaeric antibodies which contain mouse or rat antigen-binding variable (V) regions linked to human constant (C) regions. In order to construct such antibodies, a mouse or rat hybridoma specific for the desired antigen is made using the standard procedures; the expressed V region genes of the hybridoma are then isolated, joined to human C region genes by in vitro DNA recombination and a plasmid containing the genes for this chimaeric antibody is then introduced into a myeloma cell line. In this way, chimaeric human IgM, IgG or IgE antibodies have been made that are specific for TNP, phosphocholine or NP [40, 41, 31].

Methods of Cloning Immunoglobulin Genes for Expression

Rearranged Ig variable region genes can be isolated from genomic libraries of hybridomas by using the appropriate DNA probes.

In most cases the cloning strategy takes advantage of the fact that both the heavy and light chain variable regions must be joined by a J region before they can be expressed. J region probes can therefore be used to distinguish the expressed variable regions from the hundreds of non-expressed variable regions. This approach is frequently complicated by the presence of aberrantly rearranged variable regions, and a secondary assay must be used to distinguish aberrant from productive rearrangements [8]. Variable regions cloned from genomic DNA are usually expressed using their own promoter regions.

It is also possible to express rearranged V region genes that have been cloned from cDNA libraries [47, 48]. Two approaches have been used to express cDNA. In one approach the cDNAs were used to construct a variable region identical to a genomic clone with a human Ig promoter used for expression [47]. In a second approach in vitro mutagenesis was used to make the Ig region suitable for expression from an SV40 promoter [48]. Both approaches provide alternatives to genomic cloning for expression the desired variable regions.

The production of a functional antibody requires the synthesis and proper assembly of both H and L chains. For gene transfection both genes can be cloned into one vector [3]; however, this is technically difficult because of the limitation of unique restriction sites within a large plasmid. Therefore, smaller plasmids are preferable for genetic manipulations and DNA preparation.

A more practical approach has been to clone the H and L chains into two separate plasmids (FIG. 1). For example, the H chain gene is introduced into pSV2-gpt and the L chain into pSV184-neo (described above). Both plasmids are then transfected into *Escherichia coli* and amp$^R$CM$^R$ clones are isolated. Using protoplast fusion, both vectors are simultaneously transfected into the recipient cell in a single step. With the two chains on different plasmids, alterations within the gene of one chain can be made independent of the other, the transfection of different H and L chain combinations is facilitated.

It is useful to design gene 'cassettes' that make it convenient to shuffle exons of complete genes to or join a V gene to different C regions, and vice versa. For this, linkers can be used to introduce unique restricted sites in the genes. In the original vectors for the expression of chimaeric Igs, the constant regions were constructed as a SalI–BamHI cassette. In later constructions, unique PvuI sites have been placed within the intervening sequences, separating each human γ constant region domain (lower portion of FIG. 1); placing linkers within the intervening sequences avoids disrupting the translational reading frame. The presence of unique restriction sites between exons makes it much more straightforward to shuffle exons.

Ig chains have been produced in which $V_H$ is attached to $C_L$ and $V_L$ is attached to $C_H$ [49–51]. These molecules assembled, were secreted, and, when containing the appropriate variable regions, bound antigen. These light-chain heterodimers potentially provide antigen binding capacity devoid of effector function. These and similar molecules that do not occur in vivo may be modified in accordance with the invention.

II. SPECIFIC EXAMPLES

Example 1

Isolation of the Variable Domains of Clone B

Clone B is a lymphoblastoid cell line (secreting antibody directed against a tumour-associated mucin molecule) derived from the EBV-transforming and cloning of a patient's peripheral blood B-cells. After DNA isolation, the polymerase chain reaction (PCR) was employed, using oligonucleotide primers specific for the variable light and heavy chains of immunoglobulins (Table 1).

TABLE 1

Oligonucleotide Primers
For variable domain: Heavy chain ($V_H$)

| Primer name | Primer |
| --- | --- |
| $V_H$ EcoRI For | CTCGAATTCTGAGGAGACGGTGACCGTGGTCCCTTGGCCCC (SEQ ID NO 5) |
| $V_H$ Bam Back | ATCGGATCCAGGTSMARCTGCAGSAGTCWGG (SEQ ID NO 6) |

(where S = C or G, M = A or C, R = A or G and W = A or T)

The forward primer contains an EcoRI site and a BstEII site. The back primer contains a BamHI site and a PstI site.

The isolated DNA was assayed by agarose gel electrophoresis and found to be 350 base pairs in size. The DNA encoding for the $V_H$ region was gene-cleaned and ligated into a plasmid (pUC18). A single colony of TG-1 bacteria containing plasmid was isolated. This colony was expanded and a mini-prep of DNA obtained.

From this mini-prep the $V_H$ gene of the human antibody, which we now designate as clone-B, was isolated using restriction enzyme digestion. The gene encoding for the $V_H$ region was then ligated into a sequencing phage (M13mp18). TG-1 bacterial cells were transformed with phage and grown and single stranded DNA was isolated. The single stranded DNA was sequenced, using the sequenase reaction, and ran into a 6% acrylamide gel (0.4 mm thick).

Sequencing of the gene encoding the $V_H$ region of clone B provided a sequence consistent with the Kabat Human Heavy chain subgroup II classification (Table 2).

TABLE 2

HUMAN ANTI-MUCIN MoAb: DNA (SEQ ID NO 7) & AMINOACID SEQUENCE (SEQ ID NO 8)

```
                                    E   S   G   P   G   L   V
AAG ATC CAG GTC AAA CTG CAG GAG TCT GGA CCT GGC CTG GTG
  -BamHI-       --PstI--

A   P   S   Q   S   L   S   I   T   C   T   V   S   G
GCG CCC TCA CAG AGC CTG TCC ATC ACA TGC ACC GTC TCA GGG

F   S   L   T  | S   Y   G   V   H | W   V   R   Q   P
TTC TCA TTA ACT |AGC TAT GGT GTA CAC| TGG GTT CGC CAG CCT
                      CDR1

P   G   K   G   L   E   W   L  | V   V   I   W   S   D
CCA GGA AAG GGT CTG GAG TGG CTG |GTA GTG ATA TGG AGT GAT

G   S   T   T   Y   N   S   A   L   K   S | R   L   S
GGA AGC ACA ACC TAT AAT TCA GCT CTC AAA TCC|AGA CTG AGC
CDR2

I   S   K   D   N   S   K   S   Q   V   F   L   K   M
ATC AGC AAG GAC AAC TCC AAG AGC CAA GTT TTC TTA AAA ATG

N   S   L   Q   T   D   D   T   A   M   Y   Y   C   A
AAC AGT CTC CAA ACT GAT GAC ACA GCC ATG TAC TAC TGT GCC

R | E   P   P   T   T   Y   V   C   L | L   G   P   R
AGA|GAG CCT CCC ACG ACG TAC GTT TGC TTA|CTG GGG CCA AGG
          CDR3

D   T   V   T   V   S   S   E   F   V   I
GAC ACG GTC ACC GTC TCA TCA GAA TTC GTA ATC
                        --EcoRI-
```

Example 2

Isolation of the Variable Domains of NM-2

The antibody NM-2 is a murine monoclonal antibody class IgG.1, Lambda light chain, which has specificity for the mucin molecule. The antibody reacts with about 95% of epithelial tumours and cross-reacts with normal mucin.

Cloning of the variable domains of NM-2. Both the variable heavy and light chains have been cloned and sequenced using the techniques outlined in Example 1. A full list of primers and their sequences is given in Table 3.

NOTE: All primer sequences are 5'–3'

Having sequenced both the heavy ($V_H$) and light ($V_L$) chain genes for NM-2, we are now aware of all its CDR sequences (Tables 4 & 5).

TABLE 3

Primers used for the isolation and sequencing of NM-2 $V_H$ and $V_L$ genes.

Primer Name     Primer Sequence i) For variable Heavy Chain gene ($V_H$)

$V_H$ EcoR1 For   CTCGAATTCTGAGGAGACGGTGACCGTGGTCCCTTGGCCCC (SEQ ID NO 5)
$V_H$ Bam Back   ATCGGATCCAGGTSMARCTGCAGSAGTCWGG (SEQ ID NO 6)

ii) For variable light chain ($V_H$)

$V_L$ Back Eco   CAGGCTGTTGTGACTCAGGAATTCGCACTCACC (SEQ ID NO 9)
$V_L$ For Xba    ACCTAGTCTAGACAGTTTGGTTCCTCCACC (SEQ ID NO 10)

TABLE 4

DNA (SEQ ID NO 11) AND AMINO ACID SEQUENCE (SEQ ID NO 12) OF MONOCLONAL ANTIBODY NM-2 V_H DOMAIN

```
 L   Q   E   S   G   P   G   L   V   A   P   S   Q   S   L   S   I   T   C
CTGCAGGAGTCTGGACCTGGCCTGGTGGCGCCCTCACAGAGCCTGTCCATCACATGC

T   V   S   G   F   S   L   T  | S   Y   G   V   H | W   V   R   Q   P   P
ACCGTCTCAGGGTTCTCATTAACT         AGCTATGGTGTACAC     TGGGTTCGCCAGCCTCCA
                                       CDR1

G   K   G   L   E   W   L   V  | V   I   W   S   D   G   S   T   T   Y   N
GGAAAGGGTCTGGAGTGGCTGGTA         GTGATATGGAGTGATGGAAGCACAACCTATAAT
                                                  CDR2

| S   A   L   N   S | R   L   S   I   S   K   D   N   S   K   S   Q   V   F
 TCAGCTCTCAATTCC     AGACTGAGCATCAGCAAGGACAACTCCAAGAGCCAAGTTTTC

L   K   M   N   S   L   Q   T   D   D   T   A   M   Y   Y   C   A   R  | E
TTAAAAATGAACAGTCTCCAAACTGATGACACAGCCATGTACTACTGTGCCAGA                   GAG

| P   P   T   R   T   F   A   Y | W   G   Q   G
 CCTCCCACACGTACGTTTGCCTAC         TGGGGCCAAGGG
      CDR3
```

TABLE 5

NM2LAMBDA

```
|CAG GCT GTT CTG ACT CAG GAA TTC GCA CTC ACC| ACA TCA CCT
 Gln Ala Val Leu Thr Gln Glu Phe Ala Leu Thr  Thr Ser Pro 54                                   81
GGT GAA ACA GTC ACA CTC ACT TGT |CGC TCA AGT ACT GGG GCT
Gly Glu Thr Val Thr Leu Thr Cys  Arg Ser Ser Thr Gly Ala

CDR1                 108
GTT ACA ACT AGT AAC TAT GCC AAC| TGG GTC CAA GAA AAA CCA
Val Thr Thr Ser Asn Tyr Ala Asn  Trp Val Gln Glu Lys Pro 135                           162    CDR2
GAT CAT TTA CTA ACT GGT CTA ATA GGT |GGT ACC AAC AAC CGA
Asp His Leu Leu Thr Gly Leu Ile Gly  Gly Thr Asn Asn Arg

189
|GCT CCA| GGT GTT CCT GCC AGA TTC TCA GGC TCC CTG ATT GGA
 Ala Pro  Gly Val Pro Ala Arg Phe Ser Gly Ser Leu Ile Gly 216                                  243
GAC AAG GCT GCC CTC ACT ATC ACA GGG GCA CAG ACT GAG GAT
Asp Lys Ala Ala Leu Thr Ile Thr Gly Ala Gln Thr Glu Asp

270    CDR3
GAG GCA ACA TAT TTC |TGT GCT CTA TGG TAC AGC AAC CAC TGG
Glu Ala Thr Tyr Phe  Cys Ala Leu Trp Tyr Ser Asn His Trp

297
|GTG| TTC GGT GGA GGA ACC AAA CTG TCT AGA CTA GGT
 Val  Phe Gly Gly Gly Thr Lys Leu Ser Arg Leu Gly
```

Six peptides which correspond to the CDRs of NM-2's variable heavy chain have been synthesised (Table 6).

TABLE 6

CDR1A
1. Sequence NH2-SLTSYGVHWVR-COOH (SEQ ID NO 15)
CDR3A
2. Sequence NH2-YCAREPPTRTFAYWGQG-COOH (SEQ ID NO 16)
CDR3B
3. Sequence NH2-MYYCAREPPTRTFAYWGQG-COOH (SEQ ID NO 4)
CDR3D
4. Sequence NH2-EPPTRTFAY-COOH (SEQ ID NO. 2)
CDR3D
5. Sequence NH2-REPPTRTFAYWG-COOH (SEQ ID NO. 3)
CDR2A
6. Sequence NH2-WLVVIWSDGSTTYNSALNSRCM-COOH (SEQ ID NO 17)

The CDR3 peptides with the amino acid core sequence EPPT, showed antigen-binding specificity. A particularly interesting finding was that the amino acid sequence EPPT was present in the CDR3 of both murine (NM2) and human antibodies (clone B).

CDR3 grafting. The EPPT sequence was used to substitute the 5' end of CDR3 of both human and murine antibodies. These novel antibodies were shown to possess anti-mucin specificity. Thus we have shown that grafting of CDR3 alone is sufficient to endow anti-tumour specificity. This observation obviates the need for full CDR, ie CDR1 and CDR2 in addition to CDR3 grafting (as previously described by G. Winter and colleagues) in at least some cases of antibodies.

Example 3

Binding of Molecules of the Invention to Radiolabelled Mucin Peptide

Preparation of immobilised mucin receptor peptide. 7.5 mg of YVTSAPDTRPAPGST (SEQ ID No 18) (the epitope sequence from the mucin molecule) was dissolved in 100 mM sodium phosphate buffer pH8. This was mixed with 7.5 mg of bovine serum albumin (BSA) and made up to 0.5 ml with buffer. 5 μl of 25% glutaraldehye was added, mixed and left to stand at room temperature for 15 minutes. A further 2.5 μl of glutaraldehyde was then added and the mixture left for a further 15 minutes.

Following the incubation, 100 μl of 1M glycine pH6 was added and left for 10 minutes to quench the glutaraldehyde. The reaction mixture was then aliquoted into 100 μl portions and stored at −20° C. until use.

Radiolabelling of EPPT peptides prior to binding assays. Peptides were dissolved in phosphate buffered saline, 100 mM sodium phosphate pH8, or 5% DMSO in sodium phosphate. All peptides were labelled with $I^{125}$ using the Iodogen reaction. Depending on solubility up to 1 mg of peptide was radiolabelled with approximately 137 MBq of $I^{125}$ in a volume of 200 μl placed in an Iodogen tube (20 μg of Iodogen per tube) for varying times up to 60 minutes at room temperature. The Iodogen tubes were then washed with 1 ml of buffer and eluted through Sephadex G10 columns (5 ml bed volume) which had been previously equilibrated with the buffer. 1 ml fractions were collected from the eluate and assayed for radioactivity.

For example, 200 μl (1 ml) of peptide REPPTRTFAYWG (SEQ ID No 3) plus 10 μl (37 MBq) $I^{125}$ were mixed in Iodogen tube for 60 minutes at room temperature. The fractions collected from subsequent elution through a G10 column were as follows:

TABLE 7

| Fraction | Radioactivity (MBq) |
|---|---|
| Background | 0 |
| 1 | 0 |
| 2 | 2.03 |
| 3 | 8.92 |
| 4 | 6.33 |
| 5 | 4.05 |
| 6 | 3.14 |
| 7 | 2.61 |
| 8 | 2.18 |
| 9 | 1.77 |
| 10 | 1.42 |
| 11 | 1.23 |
| 12 | 0.94 |

Total activity in samples 2–12 inclusive (equivalent to 1 mg of peptide)=34.62 MBq. Therefore, sample 3=(8.92/34.62)×1 mg=0.258 mg.ml$^{-1}$.

Binding of EPPT peptides to immobilised mucin receptor peptide. The technique of equilibrium dialysis was used to determine the binding of EPPT peptides to the immobilised mucin receptor peptide. This technique utilises two chambers separated by a dialysis membrane such that small molecules (less than 12,000–14,000 daltons) are capable of freely equilibrating between the two chambers. The receptor is confined to one half of the dialysis chamber. Once the peptide has bound to its receptor, it can no longer exert an osmotic effect in the system and there is a subsequent shift in the equilibrium such that the count rate is higher in the receptor chamber than in the opposing chamber. Samples are removed from both sides of the membrane and assayed for the presence of radioactivity. For the purposes of these studies, a 1 ml dialysis module was used separated into equal parts by a dialysis membrane. Immobilised receptor peptide was added to one chamber at a final concentration of 83.3 μg (with respect to peptide). Into both chambers were added varying concentrations of the EPPT peptides and the incubation left to equilibrate for 24–48 hours at room temperature with constant rotation of the dialysis module. In addition, some modules were set up with similar concentrations of EPPT peptide (labelled with $I^{125}$), but with a ten-fold excess of unlabelled ("cold") peptide for the purpose of determining non-specific binding (nsb). Following incubation and equilibration, samples were removed from the dialysis module and counted for the presence of $I^{125}$. The radioactivity was then converted to amount of peptide for the purposes of determining the amount bound to the immobilised receptor peptide.

FIGS. 2 and 3 relate to the binding of the EPPT peptide to the mucin receptor peptide, one showing the binding of concentrations tested for each peptide whilst the bar graph shows the amount of uptake at one specific concentration of peptide for easier comparison of the four peptides so far tested. Peptide EPPTRTFAY (SEQ ID No 2) shows no real binding to the mucin receptor peptide and we believe that this reflects the fact that the charged amino group must be removed from this glutamyl residue within the binding site.

The EPPTRTFAY (SEQ ID No 2) to comprises the whole of the $V_H$ CDR-3 domain without any residues from the framework region and does not itself appear to bind the mucin receptor peptide. When three residues are added to this sequence from the adjoining framework region (ARG to N-terminus, TRP and GLY to C-terminus) binding is restored and improved by further addition of amino acid residues. We believe that the flanking residues do not have to be those from the framework region: provided the amino group of the N-terminus is distanced from the glutamic acid residue, then the molecule is capable of binding.

REFERENCES (all incorporated herein by reference)
1. Morrison, S. L. et al. *Proc. Natl. Acad. Sci. USA* 81, 6851–6855.
2. Ochi, A. et al. *Nature* (London) 302, 340–342.
3. Ochi, A. et al. *Proc. Natl. Acad. Sci. USA* 80, 6351–6355.
4. Boulianne, G. et al. *J. Mol. Biol. Med.* 4, 37–49.
5. Boulianne, G. L. et al. *Nature* (London) 312, 643–646.
6. Liu, F. R. and Gritzmacher, C. A. (1987) *J. Immunol.* 138, 324–329.
7. Sun, L. K. et al (1986) *Hybridoma* 5 (Suppl. 1), S17–S20.
8. Sahagan, B. G. et al (1986) *J. Immunol.* 137, 1066–1074.
9. Jones, P. T. et al (1985) *Nature* 321, 522–525.
10. Verhoeyen, M. et al (1988) *Science* 239, 1534–1536.
11. Riechmann, L. et al (1988) *Nature* 332, 323–327.
18. O'Sullivan et al (1979) *Anal. Biochem.* 100, 100–108.
19. Bagshawe (1987) *Br. J. Cancer* 56, 531.
20. Bagshawe et al (1988) *Br. J. Cancer* 58, 700.
21. WO 88/07378.
22. Rowlinson-Busza et al (in press, "In Vitro cytotoxicity following specific activation of amygdalin by antibody-conjugated β-glucosidase").
23. Fraker, P. J. et al (1978) *Biochem. Biophys. Res. Commun.* 80, 49–57.
24. "Monoclonal Antibodies in Immunoscintigraphy", J–F. Chatal (CRC Press, 1989).
25. Rice, D. and Baltimore, D. (1982) *Proc. Natl. Acad. Sci. USA* 79, 7862–7865.
26. Neuberger, M. S. (1983) *EMBO J.* 2, 1373–1378.
27. Ochi, A. et al (1983) *Proc. Natl. Acad. Sci. USA* 80, 6351–6355.
28. Oi, V. T. et al (1983) *Proc. Natl. Acad. Sci. USA* 80, 825–829.
29. Banerji, J. et al (1983) *Cell* 33, 729–740.
30. Gillies, S. D. et al (1983) *Cell* 33, 717–728.
31. Neuberger, M. S. et al (1985) *Nature* 314, 268–270.
32. Neuberger, M. S. and Williams G. T. (1988) *Nucl. Acids Rec.* 16.
33. Cattaneo, A. and Neuberger, M. S. (1987) *EMBO J.* 6, 2753–2758.
34. Weidle, U. H. et al (1987) *Gene* 51, 21–29.
35. Whittle, N. et al (1987) *Protein Engineering* 1, 499–505.
36. Ritchie, K. A. et al (1984) *Nature* 312, 517–521.
37. Neuberger, M. S., Caskey, H. M., Petterssen, S., Williams G. T. and Surani, M. A. (1988)
38. Skerra, A. and Plückthun, A. (1988) *Science* 240, 1038–1041.
39. Better, M. et al (1988) *Science* 240, 1041–1043.
40. Boulianne, G. L. et al (1984) *Nature* 312, 643–646.
41. Morrison, S. L. et al (1984) *Proc. Natl. Acad. Sci. USA* 81, 6851–6855.
42. Mulligan, R. C. and Berg, P. (1980) *Science* 209, 1422–1427.
43. Mulligan, R. C. and Berg, P. (1981) *Proc. Nat. Acad. Sci. USA* 78, 2072–2076.
44. Southern, P. J. and Berg, P. (1982) *J. Molec. Appl. Genet.* 1, 327–334.
45. Oi, V. T. and Morrison, S. L. (1986) *BioTechniques* 4, 214–221.
46. Deans, R. J. et al. *Proc. Natl. Acad. Sci. USA* 81, 1292–1296.
47. Morrison, S. L. et al (1987) *Ann. NY Acad. Sci.* 507, 187–198.
48. Liu, A. Y. et al (1987) *Proc. Natl. Acad. Sci. USA* 84, 3439–3443.
49. Sharon, J. et al (1984) *Nature* (London) 309, 364–367.
50. Tan, L. K. et al (1985) *J. Immunol.* 135, 3564–3567.
51. Morrison, S. L. (1985) *Science* 229, 1202–1207.
52. Taub, R. et al (1989) *J. Biol. Chem.* 264, 259–265.
53. Williams, W. V. et al (1989) *P.N.A.S. (USA)* 86, 5537–5541.
54. Winter, G. & Milstein, C. (1991) *Nature* 349, 293–299.
55. Sambrook, J. et al (1989) "*Molecular Cloning: A Laboratory Manual*" (2nd Edition), Cold Spring Harbor, N.Y., USA.
56. McCafferty, J. et al (1990) *Nature* 348, 552–554.

I claim:

1. A isolated polynucleotide encoding a molecule comprising the amino acid sequence EPPT (SEQ ID No:1), wherein the molecule is capable of binding mucin and is not the monoclonal antibody HMFG-2.

2. The isolated polynucleotide of claim 1, further comprising a compound selected from the group consisting of a radiolabel, a toxin, an enzyme, an enzyme for converting non-toxic prodrug into a cytotoxic drug, a compound for activating the immune system and a cell-stimulating compound.

3. The isolated polynucleotide of claim 2, wherein the molecule further comprises a variable region of an antibody, the amino acid sequence EPPT (SEQ ID No:1) being part of a CDR3 of the $V_H$ variable region.

4. The isolated polynucleotide of claim 2, wherein the amino acid sequence EPPT (SEQ ID No:1) is combined with additional amino acids to form a peptide of up to 30 amino acids.

* * * * *

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

Glu Pro Pro Thr
1

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

```
Glu Pro Pro Thr Arg Thr Phe Ala Tyr
1               5
```

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:3:

```
Arg Glu Pro Pro Thr Arg Thr Phe Ala Tyr Trp Gly
1               5                   10
```

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

```
Met Tyr Tyr Cys Ala Arg Glu Pro Pro Thr Arg Thr Phe Ala Tyr Trp
1               5                   10                  15
Gly Gln Gly
```

(2) INFORMATION FOR SEQ ID NO:5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

CTCGAATTCT GAGGAGACGG TGACCGTGGT CCCTTGGCCC C     41

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:6:

ATCGGATCCA GGTSMARCTG CAGSAGTCWG G     31

(2) INFORMATION FOR SEQ ID NO:7:

(i) SEQUENCE CHARACTERISTICS:
        (A) LENGTH: 369 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 22..369

(xi) SEQUENCE DESCRIPTION: SEQ ID NO:7:

```
AAGATCCAGG TCAAACTGCA G GAG TCT GGA CCT GGC CTG GTG GCG CCC TCA        51
                        Glu Ser Gly Pro Gly Leu Val Ala Pro Ser
                         1               5                  10

CAG AGC CTG TCC ATC ACA TGC ACC GTC TCA GGG TTC TCA TTA ACT AGC        99
Gln Ser Leu Ser Ile Thr Cys Thr Val Ser Gly Phe Ser Leu Thr Ser
             15                  20                  25

TAT GGT GTA CAC TGG GTT CGC CAG CCT CCA GGA AAG GGT CTG GAG TGG       147
Tyr Gly Val His Trp Val Arg Gln Pro Pro Gly Lys Gly Leu Glu Trp
         30                  35                  40

CTG GTA GTG ATA TGG AGT GAT GGA AGC ACA ACC TAT AAT TCA GCT CTC       195
Leu Val Val Ile Trp Ser Asp Gly Ser Thr Thr Tyr Asn Ser Ala Leu
         45                  50                  55

AAA TCC AGA CTG AGC ATC AGC AAG GAC AAC TCC AAG AGC CAA GTT TTC       243
Lys Ser Arg Leu Ser Ile Ser Lys Asp Asn Ser Lys Ser Gln Val Phe
     60                  65                  70

TTA AAA ATG AAC AGT CTC CAA ACT GAT GAC ACA GCC ATG TAC TAC TGT       291
Leu Lys Met Asn Ser Leu Gln Thr Asp Asp Thr Ala Met Tyr Tyr Cys
 75                  80                  85                  90

GCC AGA GAG CCT CCC ACG ACG TAC GTT TGC TTA CTG GGG CCA AGG GAC       339
Ala Arg Glu Pro Pro Thr Thr Tyr Val Cys Leu Leu Gly Pro Arg Asp
                 95                 100                 105

ACG GTC ACC GTC TCA TCA GAA TTC GTA ATC                               369
Thr Val Thr Val Ser Ser Glu Phe Val Ile
```

(2) INFORMATION FOR SEQ ID NO:8:

(i) SEQUENCE CHARACTERISTICS:
(A) LENGTH: 116 amino acids
(B) TYPE: amino acid
(D) TOPOLOGY: linear (ii) MOLECULE TYPE: protein (xi) SEQUENCE DESCRIPTION: SEQ ID NO:8:

Glu Ser Gly Pro Gly Leu Val Ala Pro Ser Gln Ser Leu Ser Ile Thr
1               5                   10                  15

Cys Thr Val Ser Gly Phe Ser Leu Thr Ser Tyr Gly Val His Trp Val
            20                  25                  30

Arg Gln Pro Pro Gly Lys Gly Leu Glu Trp Leu Val Val Ile Trp Ser
        35                  40                  45

Asp Gly Ser Thr Thr Tyr Asn Ser Ala Leu Lys Ser Arg Leu Ser Ile
50                  55                  60

Ser Lys Asp Asn Ser Lys Ser Gln Val Phe Leu Lys Met Asn Ser Leu
65                  70                  75                  80

Gln Thr Asp Asp Thr Ala Met Tyr Tyr Cys Ala Arg Glu Pro Pro Thr
                85                  90                  95

Thr Tyr Val Cys Leu Leu Gly Pro Arg Asp Thr Val Thr Val Ser Ser
            100                 105                 110

Glu Phe Val Ile
        115

(2) INFORMATION FOR SEQ ID NO:9:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CAGGCTGTTG TGACTCAGGA ATTCGCACTC ACC                                33

(2) INFORMATION FOR SEQ ID NO:10:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:10:

ACCTAGTCTA GACAGTTTGG TTCCTCCACC                                    30

(2) INFORMATION FOR SEQ ID NO:11:

(i) SEQUENCE CHARACTERISTICS:
            (A) LENGTH: 321 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: CDS
            (B) LOCATION: 1..321

(xi) SEQUENCE DESCRIPTION: SEQ ID NO:11:

```
CTG CAG GAG TCT GGA CCT GGC CTG GTG GCG CCC TCA CAG AGC CTG TCC      48
Leu Gln Glu Ser Gly Pro Gly Leu Val Ala Pro Ser Gln Ser Leu Ser
 1               5                  10                  15

ATC ACA TGC ACC GTC TCA GGG TTC TCA TTA ACT AGC TAT GGT GTA CAC      96
Ile Thr Cys Thr Val Ser Gly Phe Ser Leu Thr Ser Tyr Gly Val His
                20                  25                  30

TGG GTT CGC CAG CCT CCA GGA AAG GGT CTG GAG TGG CTG GTA GTG ATA     144
Trp Val Arg Gln Pro Pro Gly Lys Gly Leu Glu Trp Leu Val Val Ile
             35                  40                  45

TGG AGT GAT GGA AGC ACA ACC TAT AAT TCA GCT CTC AAT TCC AGA CTG     192
Trp Ser Asp Gly Ser Thr Thr Tyr Asn Ser Ala Leu Asn Ser Arg Leu
 50                  55                  60

AGC ATC AGC AAG GAC AAC TCC AAG AGC CAA GTT TTC TTA AAA ATG AAC     240
Ser Ile Ser Lys Asp Asn Ser Lys Ser Gln Val Phe Leu Lys Met Asn
 65                  70                  75                  80

AGT CTC CAA ACT GAT GAC ACA GCC ATG TAC TAC TGT GCC AGA GAG CCT     288
Ser Leu Gln Thr Asp Asp Thr Ala Met Tyr Tyr Cys Ala Arg Glu Pro
                 85                  90                  95

CCC ACA CGT ACG TTT GCC TAC TGG GGC CAA GGG                         321
Pro Thr Arg Thr Phe Ala Tyr Trp Gly Gln Gly
                100                 105
```

(2) INFORMATION FOR SEQ ID NO:12:

(i) SEQUENCE CHARACTERISTICS:
            (A) LENGTH: 107 amino acids
            (B) TYPE: amino acid
            (D) TOPOLOGY: linear (ii) MOLECULE TYPE: protein (xi) SEQUENCE DESCRIPTION: SEQ ID NO:12:

```
Leu Gln Glu Ser Gly Pro Gly Leu Val Ala Pro Ser Gln Ser Leu Ser
 1               5                  10                  15

Ile Thr Cys Thr Val Ser Gly Phe Ser Leu Thr Ser Tyr Gly Val His
                20                  25                  30

Trp Val Arg Gln Pro Pro Gly Lys Gly Leu Glu Trp Leu Val Val Ile
             35                  40                  45

Trp Ser Asp Gly Ser Thr Thr Tyr Asn Ser Ala Leu Asn Ser Arg Leu
 50                  55                  60

Ser Ile Ser Lys Asp Asn Ser Lys Ser Gln Val Phe Leu Lys Met Asn
 65                  70                  75                  80

Ser Leu Gln Thr Asp Asp Thr Ala Met Tyr Tyr Cys Ala Arg Glu Pro
                 85                  90                  95

Pro Thr Arg Thr Phe Ala Tyr Trp Gly Gln Gly
                100                 105
```

(2) INFORMATION FOR SEQ ID NO:13:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
       (A) NAME/KEY: CDS
       (B) LOCATION: 1..330

(xi) SEQUENCE DESCRIPTION: SEQ ID NO:13:

```
CAG GCT GTT CTG ACT CAG GAA TTC GCA CTC ACC ACA TCA CCT GGT GAA        48
Gln Ala Val Leu Thr Gln Glu Phe Ala Leu Thr Thr Ser Pro Gly Glu
  1               5                  10                  15

ACA GTC ACA CTC ACT TGT CGC TCA AGT ACT GGG GCT GTT ACA ACT AGT        96
Thr Val Thr Leu Thr Cys Arg Ser Ser Thr Gly Ala Val Thr Thr Ser
             20                  25                  30

AAC TAT GCC AAC TGG GTC CAA GAA AAA CCA GAT CAT TTA CTA ACT GGT       144
Asn Tyr Ala Asn Trp Val Gln Glu Lys Pro Asp His Leu Leu Thr Gly
         35                  40                  45

CTA ATA GGT GGT ACC AAC AAC CGA GCT CCA GGT GTT CCT GCC AGA TTC       192
Leu Ile Gly Gly Thr Asn Asn Arg Ala Pro Gly Val Pro Ala Arg Phe
     50                  55                  60

TCA GGC TCC CTG ATT GGA GAC AAG GCT GCC CTC ACT ATC ACA GGG GCA       240
Ser Gly Ser Leu Ile Gly Asp Lys Ala Ala Leu Thr Ile Thr Gly Ala
 65                  70                  75                  80

CAG ACT GAG GAT GAG GCA ACA TAT TTC TGT GCT CTA TGG TAC AGC AAC       288
Gln Thr Glu Asp Glu Ala Thr Tyr Phe Cys Ala Leu Trp Tyr Ser Asn
                 85                  90                  95

CAC TGG GTG TTC GGT GGA GGA ACC AAA CTG TCT AGA CTA GGT               330
His Trp Val Phe Gly Gly Gly Thr Lys Leu Ser Arg Leu Gly
                100                 105                 110
```

(2) INFORMATION FOR SEQ ID NO:14:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO:14:

```
Gln Ala Val Leu Thr Gln Glu Phe Ala Leu Thr Thr Ser Pro Gly Glu
  1               5                  10                  15

Thr Val Thr Leu Thr Cys Arg Ser Ser Thr Gly Ala Val Thr Thr Ser
             20                  25                  30

Asn Tyr Ala Asn Trp Val Gln Glu Lys Pro Asp His Leu Leu Thr Gly
         35                  40                  45

Leu Ile Gly Gly Thr Asn Asn Arg Ala Pro Gly Val Pro Ala Arg Phe
     50                  55                  60

Ser Gly Ser Leu Ile Gly Asp Lys Ala Ala Leu Thr Ile Thr Gly Ala
 65                  70                  75                  80

Gln Thr Glu Asp Glu Ala Thr Tyr Phe Cys Ala Leu Trp Tyr Ser Asn
                 85                  90                  95
```

```
His Trp Val Phe Gly Gly Gly Thr Lys Leu Ser Arg Leu Gly
            100                 105                 110
```

(2) INFORMATION FOR SEQ ID NO:15:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:15:

```
Ser Leu Thr Ser Tyr Gly Val His Trp Val Arg
1               5                   10
```

(2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:16:

```
Tyr Cys Ala Arg Glu Pro Pro Thr Arg Thr Phe Ala Tyr Trp Gly Gln
1               5                   10                  15
Gly
```

(2) INFORMATION FOR SEQ ID NO:17:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:17:

```
Trp Leu Val Val Ile Trp Ser Asp Gly Ser Thr Thr Tyr Asn Ser Ala
1               5                   10                  15
Leu Asn Ser Arg Cys Met
            20
```

(2) INFORMATION FOR SEQ ID NO:18:

(i) SEQUENCE CHARACTERISTICS:
        (A) LENGTH: 15 amino acids

```
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

Tyr Val Thr Ser Ala Pro Asp Thr Arg Pro Ala Pro Gly Ser Thr
1               5                  10                  15
```